United States Patent
Ewing et al.

(10) Patent No.: US 9,724,497 B2
(45) Date of Patent: Aug. 8, 2017

(54) METHOD OF COATING A CATHETER BALLOON HAVING A FOLD

(71) Applicant: Bayer Intellectual Property GmbH, Monheim (DE)

(72) Inventors: Benjamin T. Ewing, Wexford, PA (US); Gregory G. Brucker, Minneapolis, MN (US); Scott A. Bednar, Freedom, PA (US); John R. Periard, North Huntingdon, PA (US); Ashok A. Sharma, Hopkins, MN (US); Steven D. Savage, Paynesville, MN (US); Arthur E. Uber, Pittsburgh, PA (US); Brian P. Dickerson, Mt. Pleasant, PA (US)

(73) Assignee: Bayer Intellectual Property GmbH, Monheim (DE)

( * ) Notice: Subject to any disclaimer, the term of this patent is extended or adjusted under 35 U.S.C. 154(b) by 0 days.

(21) Appl. No.: 14/808,099

(22) Filed: Jul. 24, 2015

(65) Prior Publication Data

US 2015/0352340 A1 Dec. 10, 2015

Related U.S. Application Data

(62) Division of application No. 12/990,157, filed as application No. PCT/US2009/042521 on May 1, 2009, now Pat. No. 9,126,025.

(Continued)

(51) Int. Cl.
*A61M 25/10* (2013.01)
*A61L 29/08* (2006.01)
(Continued)

(52) U.S. Cl.
CPC ........... *A61M 25/104* (2013.01); *A61B 17/22* (2013.01); *A61L 29/08* (2013.01); *A61L 29/16* (2013.01);
(Continued)

(58) Field of Classification Search
CPC .. A61F 2/013; A61F 2/02; A61F 2/844; A61F 2002/823; A61L 29/00;
(Continued)

(56) References Cited

U.S. PATENT DOCUMENTS 4,824,436 A * 4/1989 Wolinsky ............... A61B 17/22
604/101.03
4,994,033 A * 2/1991 Shockey ................... A61F 2/82
604/101.02

(Continued)

FOREIGN PATENT DOCUMENTS

AU 2002241676 B2 * 9/2003
AU 2003 269 690 A1 4/2004
(Continued)

OTHER PUBLICATIONS

Park S. et al. "Surface Modification of Poly(ethylene Terephthalate) Angioplast Balloons With a Hydrophilic Poly (Acrylamide-Co-Ethylene Glycol) Interpenetrationg Polymer Network Coating" Division of Biological Materials, Norhtwestern Univeristy Medical School, J Biomed Mater Res. (2000); 53(5); 568-76.

(Continued)

*Primary Examiner* — Carl Arbes

(57) ABSTRACT

Various methods for optimizing coating of medical devices, such as balloon catheters are disclosed. One method configures catheter balloon folds based on balloon diameter and volume. Other methods include using a specifically-sized protective sheath, using a vacuum, using pressure, pulling the balloon through a coating solution, using at least one (Continued)

spacer or a wick between at least one fold for metering a therapeutic coating into the folds of the balloon, placing an intermediate layer between the balloon and the therapeutic coating, placing a soluble film having a therapeutic agent around the catheter balloon or inside the folds, and any combination thereof. Balloon catheters and catheter balloons having a specific folding configuration, a specifically-sized protective sheath, an intermediate layer, or a soluble film are also disclosed.

5 Claims, 14 Drawing Sheets

Related U.S. Application Data

(60) Provisional application No. 61/049,448, filed on May 1, 2008.

(51) Int. Cl.
*A61B 17/22* (2006.01)
*A61L 29/16* (2006.01)

(52) U.S. Cl.
CPC .... *A61M 25/1002* (2013.01); *A61M 25/1029* (2013.01); *A61M 25/1038* (2013.01); *A61B 2017/22001* (2013.01); *A61B 2017/22051* (2013.01); *A61B 2017/22061* (2013.01); *A61L 2420/02* (2013.01); *A61M 2025/1004* (2013.01); *A61M 2025/105* (2013.01); *A61M 2025/1031* (2013.01); *A61M 2025/1075* (2013.01); *A61M 2210/12* (2013.01); *Y10T 29/49826* (2015.01)

(58) Field of Classification Search
CPC ...... A61L 29/08; A61L 29/16; A61L 2420/02; A61B 17/22; A61B 2017/22001; A61B 2017/22051; A61B 2017/220061; A61M 25/104; A61M 25/1002; A61M 25/1029; A61M 25/1038; A61M 2025/105; A61M 2025/1004; A61M 2025/1031; A61M 2025/1075; A61M 2210/12; Y10T 29/49826

See application file for complete search history.

(56) References Cited

U.S. PATENT DOCUMENTS

| | | | |
|---|---|---|---|
| 5,102,402 A * | 4/1992 | Dror | A61F 2/958 604/103.02 |
| 5,120,322 A * | 6/1992 | Davis | A61K 31/195 128/898 |
| 5,304,121 A | 4/1994 | Sahatijian | |
| 5,318,587 A | 6/1994 | Davey | |
| 5,324,261 A | 6/1994 | Admunson et al. | |
| 5,370,614 A | 12/1994 | Admunson et al. | |
| 5,470,307 A * | 11/1995 | Lindall | A61L 29/14 600/339 |
| 5,509,899 A | 4/1996 | Fan et al. | |
| 5,609,629 A | 3/1997 | Fearnot et al. | |
| 5,628,730 A | 5/1997 | Shapland et al. | |
| 5,738,901 A | 4/1998 | Wang et al. | |
| 5,916,596 A | 6/1999 | Desai et al. | |
| 5,951,586 A * | 9/1999 | Berg | A61F 2/07 606/198 |
| 5,964,223 A * | 10/1999 | Baran | A61M 16/0463 128/200.14 |
| 6,039,721 A | 3/2000 | Johnson et al. | |
| 6,254,921 B1 | 7/2001 | Chappa et al. | |
| 6,306,166 B1 | 10/2001 | Barry et al. | |
| 6,326,395 B1 | 12/2001 | Tidwele et al. | |
| 6,364,856 B1 | 4/2002 | Ding et al. | |
| 6,406,754 B2 | 6/2002 | Chappa et al. | |
| 6,447,835 B1 | 9/2002 | Wang et al. | |
| 6,656,517 B2 | 12/2003 | Michal et al. | |
| 6,740,678 B2 | 5/2004 | Moulton et al. | |
| 6,743,462 B1 | 6/2004 | Pacetti | |
| 6,918,927 B2 | 7/2005 | Bates et al. | |
| 7,037,552 B2 | 5/2006 | Zhong et al. | |
| 7,060,051 B2 | 6/2006 | Palasis | |
| 7,115,299 B2 | 10/2006 | Kohish | |
| 7,306,616 B2 | 12/2007 | Eidenschink et al. | |
| 7,306,625 B1 | 12/2007 | Stratford et al. | |
| 7,323,210 B2 | 1/2008 | Castro et al. | |
| 7,371,424 B2 | 5/2008 | Schwarz | |
| 7,455,876 B2 | 11/2008 | Castro et al. | |
| 7,485,334 B2 | 2/2009 | Kerrigan | |
| 7,803,149 B2 | 9/2010 | Bates et al. | |
| 8,001,922 B2 | 8/2011 | Labrecque et al. | |
| 8,597,720 B2 | 12/2013 | Hoffmann et al. | |
| 2002/0098278 A1 | 7/2002 | Bates et al. | |
| 2003/0130717 A1 | 7/2003 | Hale et al. | |
| 2003/0161937 A1 | 8/2003 | Leiby et al. | |
| 2003/0207022 A1 | 11/2003 | Shekalim et al. | |
| 2004/0006305 A1 * | 1/2004 | Hebert | A61M 25/0021 604/96.01 |
| 2004/0044405 A1 * | 3/2004 | Wolff | A61L 31/16 623/1.46 |
| 2005/0015105 A1 | 1/2005 | Tang et al. | |
| 2005/0058768 A1 | 3/2005 | Teichman | |
| 2005/0278021 A1 | 12/2005 | Bates et al. | |
| 2006/0020243 A1 | 1/2006 | Speck et al. | |
| 2006/0112536 A1 | 1/2006 | Herweck et al. | |
| 2006/0030936 A1 | 2/2006 | Weber et al. | |
| 2006/0034883 A1 * | 2/2006 | Dang | A61F 2/07 424/422 |
| 2006/0067974 A1 | 3/2006 | Labrecque et al. | |
| 2006/0121081 A1 | 6/2006 | Labrecque et al. | |
| 2006/0182873 A1 | 8/2006 | Klisch et al. | |
| 2006/0217801 A1 | 9/2006 | Rosenthal et al. | |
| 2006/0251824 A1 | 11/2006 | Boulais et al. | |
| 2007/0032865 A1 | 2/2007 | Otis et al. | |
| 2007/0184093 A1 | 8/2007 | Hang | |
| 2007/0282419 A1 | 12/2007 | Hilaire et al. | |
| 2008/0095921 A1 | 4/2008 | O'Connor et al. | |
| 2008/0171130 A1 | 7/2008 | Merritt et al. | |
| 2008/0286440 A1 | 11/2008 | Scheer | |
| 2009/0047414 A1 | 2/2009 | Corbell et al. | |
| 2009/0054837 A1 | 2/2009 | Von Holst et al. | |
| 2009/0136560 A1 | 5/2009 | Bates et al. | |
| 2009/0227949 A1 | 9/2009 | Knapp et al. | |

FOREIGN PATENT DOCUMENTS

| | | |
|---|---|---|
| DE | 10 2004 048265 A1 | 4/2006 |
| DE | 10 2005 039126 A1 | 2/2007 |
| EP | 0935973 | 8/1999 |
| EP | 1468660 | 10/2004 |
| EP | 1917986 | 5/2008 |
| JP | 8047539 | 2/1996 |
| JP | 2008284019 | 11/2008 |
| WO | WO9625176 | 8/1996 |
| WO | WO9731674 | 9/1997 |
| WO | WO9814174 | 4/1998 |
| WO | WO9836784 | 8/1998 |
| WO | WO0002184 | 4/2000 |
| WO | WO0032267 | 6/2000 |
| WO | WO0045744 | 10/2000 |
| WO | WO0124866 | 4/2001 |
| WO | WO01/49268 | 7/2001 |
| WO | WO02076509 | 10/2002 |
| WO | WO03090684 | 6/2003 |
| WO | WO2004028582 | 8/2004 |
| WO | WO2005105321 | 11/2005 |
| WO | WO2006023104 | 3/2006 |
| WO | WO2006037049 | 4/2006 |
| WO | WO2007067215 | 6/2007 |
| WO | WO2007090385 | 8/2007 |
| WO | WO2008021013 | 2/2008 |
| WO | WO2008021019 | 2/2008 |

(56) References Cited

FOREIGN PATENT DOCUMENTS

| WO | WO2008051339 | 5/2008 |
|----|--------------|--------|
| WO | WO2008060877 | 5/2008 |
| WO | WO2008086794 | 7/2008 |
| WO | WO2009018816 | 2/2009 |

OTHER PUBLICATIONS

Winters, W.J. et al. "Reduction in Ischemic Vascular Complications With a Hydrophilic-Coated Intra-Aortic Ballon Catheter" Cardiovascular Division, Washington University School of Medicine, Catheter Cardiovasc Interv, (1999); 46(3); 357-62.

European Search Report for European Application No. 16195148.8, Mar. 28, 2017, 10 pages.

\* cited by examiner

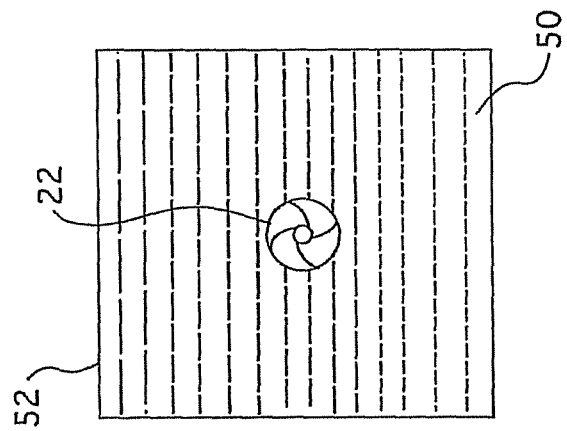
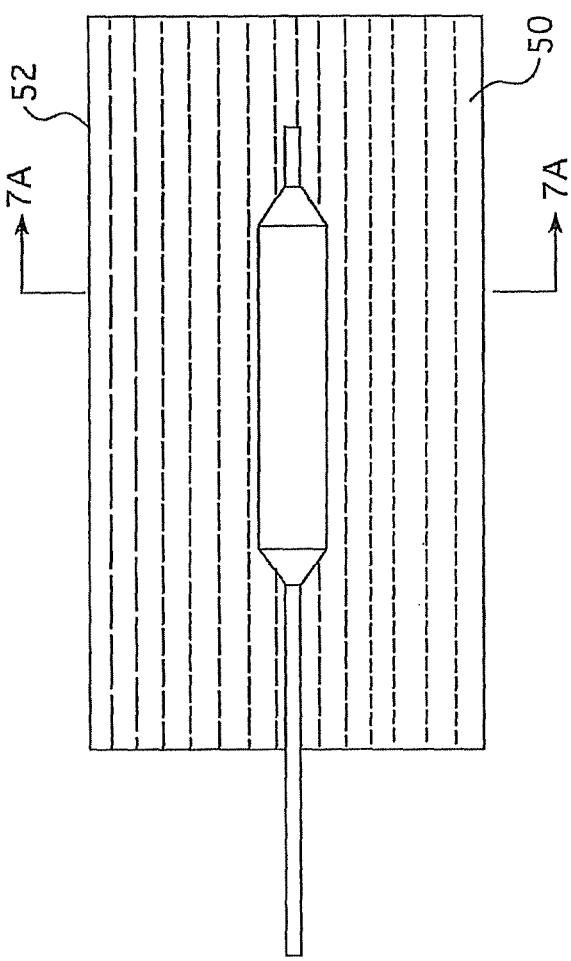
FIG. 7B
FIG. 7A

METHOD OF COATING A CATHETER BALLOON HAVING A FOLD

CROSS REFERENCE TO RELATED APPLICATION

This application is a Division of and claims the benefit of U.S. patent application Ser. No. 12/990,157, filed Dec. 15, 2010, which claims priority to U.S. National Stage application No. PCT/US2009/42521 filed May 1, 2009, which claims priority to U.S. Provisional Patent Application No. 61/049,448 filed on May 1, 2008.

FIELD OF THE DISCLOSURE

Embodiments of the present disclosure generally relate to coated medical devices and methods for coating medical devices. More particularly, embodiments of the present disclosure relate to percutaneous transluminal angioplasty balloon catheters coated with a therapeutic agent and methods for coating percutaneous transluminal angioplasty catheter balloons.

BACKGROUND

The following background information is provided to assist the reader to understand embodiments disclosed below and the environment in which they may be used. The terms used herein are not intended to be limited to any particular narrow interpretation unless clearly stated otherwise, either expressly or impliedly, in this document.

Medical devices, such as percutaneous transluminal angioplasty (PTA) balloon catheters, are often coated with various agents, including for example therapeutic agents, radiopaque materials, lubricious materials, hydrophilic materials, and biocompatible materials. PTA is a medical procedure that is used to reduce or eliminate blockages within the vascular system in order to relieve clinical symptoms associated with reduced blood flow to an organ or region of the body. PTA works by placing a non-elastomeric balloon within a blockage or narrowing and inflating it with sufficient force to restore blood flow to the distal anatomy. The balloon both compresses and expands the atherosclerotic plaque to effectively enlarge a previously constricted lumen. This procedure has become a primary therapy for treatment of occlusive vascular disease.

Unfortunately, PTA has a very high incidence of restenosis, sometimes exceeding 50%. In some circumstances, a bare metal stent (BMS) or a drug eluting stent (DES) is placed at the site of the plaque after PTA to prevent restenosis. A BMS reduces the incidence of restenosis to approximately 20% and although DES's are not currently approved for the peripheral arteries, a DES can reduce restenosis to less than 5% in the coronary arteries. While a DES is the preferred method of treatment of occlusive vascular disease (OVD) in the coronary arteries currently, problems related to late restenosis and late in-stent thrombosis have been noted with DES. In addition, the patient must remain on antiplatelet and anticoagulant therapy for an extended period of time after the procedure. Therefore, there is a need for alternate or improved therapies for the treatment of OVD. Recent therapies involve the use of drug coated PTA catheter balloons, with or without a bare metal stent, for the delivery of the drug at the lesion site to prevent restenosis.

Standard methods for coating PTA catheter balloons, such as dip coating, have several drawbacks. For example, the coating is inconsistent, non-uniform, and shreds away during handling. In addition, the process is very labor intensive, lengthy, and environmentally unfriendly. Thus, there is a continued need for improved PTA catheter balloons and methods of coating catheter balloons providing uniform and consistent delivery of effective dosages of therapeutic agents to target locations with reduced systemic dosages as well as reduced manufacturing costs.

SUMMARY

In general, various embodiments of the present disclosure are directed to methods for optimizing coating of medical devices, such as balloon catheters, including metered and consistent concentrations of therapeutic agents. Various embodiments of the present disclosure are also directed to catheter balloons and PTA catheters with optimized coating features.

In one embodiment, a method of folding a catheter balloon for optimizing coating of the balloon is disclosed. The number of folds is configured for a specific balloon diameter and a volume of coating composition necessary to achieve a target concentration, such as a therapeutic agent target concentration. A balloon catheter and a folded catheter balloon with a specific number of folds based on the balloon diameter and volume are also disclosed.

In another embodiment, a substantially specifically-sized protective sheath for a given balloon diameter with optional spiral slits is disclosed. The specifically-sized protective sheath may be placed over the balloon before or after coating of the balloon. The specifically-sized protective sheath aids in metered methods of coating catheter balloons as well as coating distribution and protection.

Various embodiments related to optimizing coating of catheter balloons include using a vacuum, pressure, pulling the balloon through a coating solution, optimization of the concentration of a therapeutic coating solution, using at least one spacer or a wick within at least one fold for metering the coating solution into the folds of the balloon, placing an intermediate layer between the balloon and the coating, placing a soluble film comprising a therapeutic agent around the catheter balloon or inside the folds, and any combination thereof. In additional embodiments, balloon catheters and catheter balloons having an intermediate layer or a soluble film are disclosed.

Those and other details, objects, and advantages of the present disclosure will become better understood or apparent from the following description and drawings showing embodiments thereof.

BRIEF DESCRIPTION OF THE DRAWINGS

The accompanying drawings illustrate examples of embodiments of the disclosure. In such drawings:

FIG. 7A and FIG. 7B depict a balloon catheter in a pressurized chamber for pressurized dip coating (FIG. 7A) and a cross-sectional view of the folded balloon in the pressurized chamber at position 7A-7A (FIG. 7B);

DESCRIPTION

Figure 1:
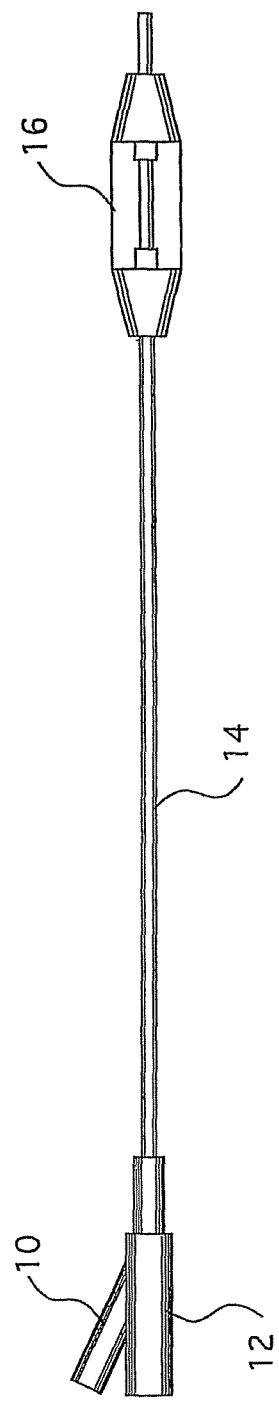
FIG. 1 is a general schematic diagram of a PTA balloon catheter.

In all of its embodiments and related aspects, the present disclosure may be used with medical devices, including, for example, PTA balloon catheters. Other examples of medical devices include, without limitation, drainage catheters, replacement or artificial venous valves, aortic valves, replacement valves, ventricular catheters, ventriculostomy balloons, balloon expandable stents, and coronary balloons.

Medical devices are routinely coated with compositions including, for example and without limitation, therapeutic agents, radiopaque materials, radioactive materials, polymeric materials, sugars, waxes, fats, and lubricious materials. As used herein, "therapeutic agent" includes, but is not limited to, any therapeutic, for example drugs, genetic material, and biological material. Genetic material includes for example, without limitation, DNA or RNA, viral vectors and non-viral vectors. Biological material includes for example, without limitation, cells, bacteria, proteins such as growth factors, peptides, lipids, and hormones. Drugs include, without limitation, anti-thrombogenic agents, anti-proliferative agents, anti-inflammatory agents, anti-neoplastic agents such as epothilone and its derivatives, antimiotic agents, antioxidants, anti-coagulants, immunosuppressants such as sirolimus and its derivatives, vascular cell growth promoters, vascular cell growth inhibitors, antibiotic agents, angiogenic substances, restenosis-inhibiting agents, and drugs for heart failure. The "therapeutic agent" may include a combination of one or more therapeutics. Particular embodiments include restenosis-inhibiting agents such as Taxol, paclitaxel, paclitaxel analogues, derivatives, and mixtures thereof. The coatings can be in solid, liquid, or gas forms depending on the method used to coat the device. In an example, carriers may be used with the therapeutic, such as, for example and without limitation, bioabsorbable agents, microspheres, microtubes, and physiologically compatible non-reactive drug transfer or radio opaque agents, such as urea, iopromide, cremophore EL, vitamin E, Tocopheryl Polyethylene Glycol Succinate (TPGS), etc.

Various embodiments described herein pertain to a PTA catheter balloon that has a specialized coating containing a therapeutic agent. The PTA catheter balloon both dilates a stenotic lesion and simultaneously impregnates a therapeutic agent into the vascular wall during inflation. In another embodiment, the present disclosure is particularly useful in treatment of peripheral vascular disease in vessels with long, diffuse lesions, such as iliac, femoropopliteal, and tibial/below the knee arteries.

Peripheral vascular disease has several distinguishing characteristics from its coronary counterpart even though the underlying atherosclerotic process is similar. First, the peripheral vasculature can range in diameter from 12 mm for iliac to less than 2 mm for tibial arteries compared to coronary which can range from 1.5-4 mm. For most peripheral vascular disease, the lesions are longer and more diffuse whereas for coronary artery disease, they are shorter and more focal. Also, the location of the target arteries is more variable, resulting in different length catheters. In addition, stents are particularly problematic in peripheral vasculature due to stent fractures and low long term patency rates. Other applicable vasculatures include renal, which has a diameter of about 4-7 mm and a length of about 15-40 mm, and intracranial, which has a diameter of about 1-3 mm and a length of about 5-30 mm.

Embodiments of the present disclosure pertain to both over-the-wire and rapid exchange PTA catheters. FIG. 1 is a general schematic of a PTA catheter including, without limitation, an inflation lumen 10, a guidewire lumen 12, a shaft 14, and a balloon 16. Various embodiments of the present disclosure relate to methods for applying and adhering a coating containing a therapeutic agent to catheter balloons 16 used generally in all angioplasty procedures, including balloon expandable stents.

The embodiments herein are not designed to be limiting but could be combined with other adherence techniques including, for example and without limitation, electrodepositing, pad printing, microspheres, nanotubes, dipping, spraying, brushing, powdering, dusting, vaporization, dripping, injecting, electrical activation of drug release, plasma treating, etc. The embodiments described herein can include coating compositions in a liquid, solid, gas, gel, slurry, etc. state as appropriate. Further, the embodiments described herein may be utilized at any appropriate stage of balloon 16 manufacturing including, for example, extrusion, blow-molding, pleating, folding, after folding, and before or after placement of a protective sheath.

Various embodiments of the present disclosure pertain to an adherent coating containing a therapeutic agent on the balloon 16 for inhibiting restenosis after angioplasty. As an example, the coating is a blend of iopromide and paclitaxel dissolved in solvents with minimal to no amounts of water to form a solution which is then applied to the balloon 16. Solvents include, for example and without limitation, methanol, ethanol, acetone, isopropanol, methyl ethyl ketone, ethyl acetate, butyl acetate, butyl chloride, chloroform, diethyl ether, dimethyl sulfoxide, dimethyl formamide, tetrahydrofuran, glycerin, essential oils, water, mixtures thereof, etc. For example, the target concentration average drug range for paclitaxel is about 0.5-10.5 micrograms/mm$^2$ of total balloon 16 surface area, more preferably about 2-6 micrograms/mm$^2$, and more preferably about 3±10% micrograms/mm$^2$. The coating is dynamically released upon inflation of the balloon 16 and transferred to the arterial wall. After deflation, the drug remains impregnated in arterial tissue to inhibit restenosis.

Dip coating may be used to coat catheter balloons 16. Dip coated balloon catheters have a coating on the surface of the balloon 16 applied by immersing the balloon 16 into a coating solution containing at least one solvent and a therapeutic, such as, for example, Paclitaxel and a transfer agent, such as Ultravist 370® contrast media as manufactured by Bayer Schering Pharma. The external surface of the balloon 16 and the internal surfaces of the folds of the balloon 16 are exposed to the coating solution, filling the interstitial spaces of the folds under the action of surface tension and gravity and coating the outside surfaces under the action of surface tension. The balloon 16 is then removed from the solution and excess solution allowed to drain, after which the solution is allowed to dry on the balloon 16 surfaces. In general, this process is not capable of applying a uniform and quantitatively reproducible coating on the balloon 16 surface and multiple dippings may be required to increase the therapeutic concentration to its desired level.

To address these issues, embodiments of the present disclosure or combinations thereof provide for metering a specific amount of a therapeutic agent into the folds and/or onto the surface of the balloon 16. As an example, the embodiments disclosed herein with or without modification of the coating solution may enhance the standard dipping method to allow a single step process.

Embodiments of the present disclosure include a metered injection process in which a predetermined amount of coating solution is applied to a folded balloon 16 at one time, after which a protective sheath is placed over the coated balloon 16. In one embodiment, an injection device, such as, for example and without limitation, a precision glass syringe 18, a pipette, a nozzle, etc., is filled with the exact amount of coating solution required to achieve the desired concentration of a therapeutic on the balloon 16. If necessary, the injection device could be refilled from a reservoir and additional coating solution added. In an alternative, the concentration of the therapeutic in the coating solution is optimized. For examples using a syringe, see FIG. 2 and FIG. 3. The needle 20 of the syringe 18 is placed in close proximity to the balloon 16 surface and the coating solution is applied to the balloon 16 by depressing a plunger and moving the needle 20 over the surface of the balloon 16 to be coated. Once all required coating solution is applied to the balloon 16, the balloon 16 is rotated for a short period of time to obtain a uniform distribution of coating solution over the coated surfaces and to allow the surface coating to partially dry. A protective sheath (not shown in FIG. 2 and FIG. 3) may be placed over the balloon 16 and the remaining liquid solution is distributed in the folds and the solution allowed to dry over time.

Figure 2:
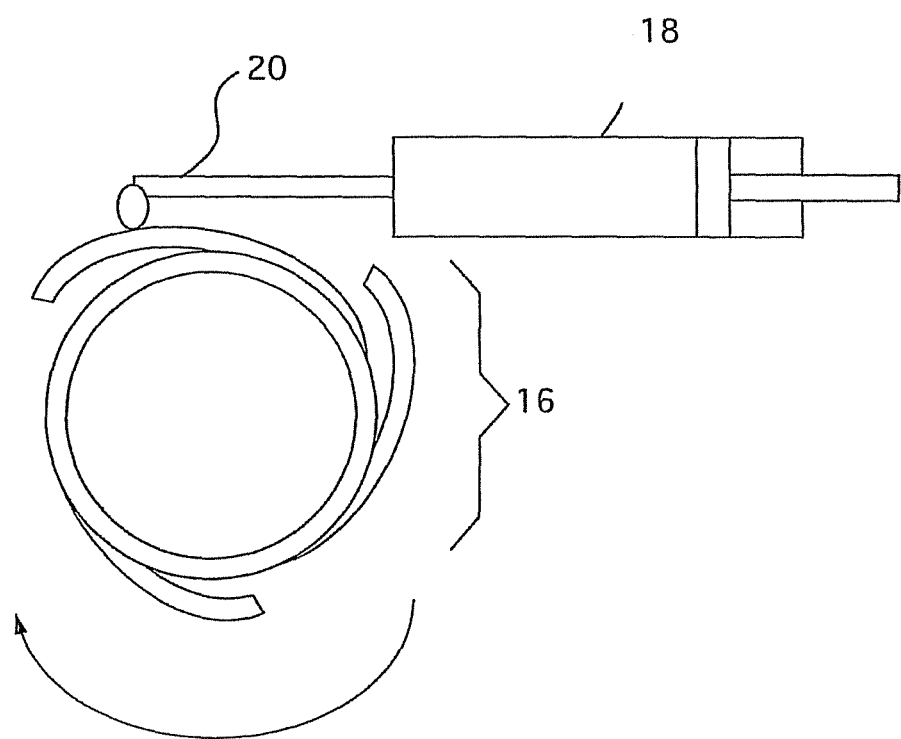
FIG. 2 depicts an injection method for coating the outside surface of a catheter balloon.
Figure 3:
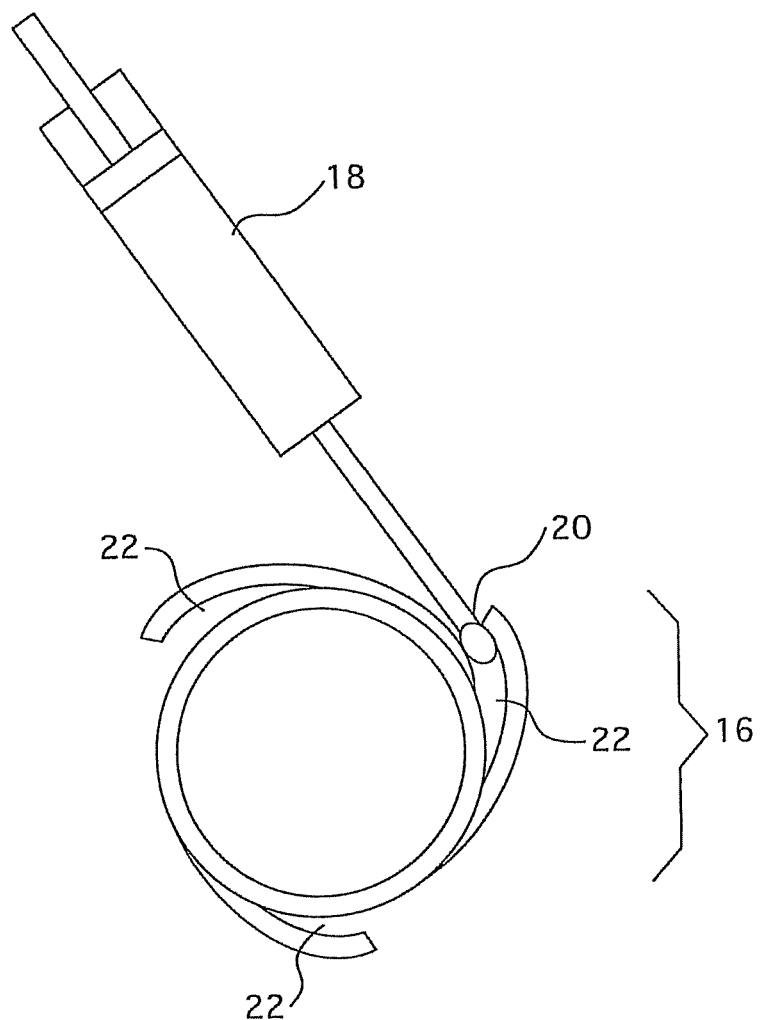
FIG. 3 depicts an injection method for coating inside a catheter balloon fold.

In further examples, two metered injection techniques for applying solution to folded balloons 16 to produce different coating distributions on the balloon 16 are disclosed. In the first technique, outside surfaces of a balloon 16 are coated uniformly by holding a syringe needle 20, for example, horizontally with the tip just slightly above but not touching the balloon 16 as shown in FIG. 2. The balloon 16 is rotated continuously while solution is applied to the balloon 16 and the syringe needle 20 moved axially along the balloon 16 length. Surface tension wicks the coating solution from the syringe needle 20 onto the balloon 16. In the second technique, internal surfaces of balloon folds 22 are coated by holding a syringe needle 20 vertically with its tip at the entrance to the fold 22 as shown in FIG. 3. Coating solution is applied into the folds 22 while the syringe needle 20 is moved axially along the entrance to the fold 22. For balloons 16 with multiple folds 22, the balloon 16 is then indexed to the next fold 22 and the process repeated until all folds 22 have been filled. As an alternative, multiple injection devices may be used to fill all the folds 22 at one time. At the completion of either technique, the balloon 16 is rotated for a short period of time to ensure uniform distribution of the coating solution in the folds 22 and/or partial drying of the surface coating. These two techniques can be combined to produce a coating distribution over both internal and external surfaces of a folded balloon 16. These methods, used separately or in combination, provide the ability to control both the amount of coating solution, i.e. therapeutic, and the location on a folded balloon 16.

Embodiments of the present disclosure can utilize technology to meter nanoliter droplets onto the surface of a balloon 16 in a predefined pattern. The technology works by using piezoelectric pressure pulses to force liquid through a small, precision orifice to create tiny droplets that are expelled onto a surface. By controlling the magnitude of the pressure pulse, the size of a fluid droplet can be controlled very accurately. In this embodiment, coating solution fills a small chamber and an electrical signal is sent to a piezoelectric crystal, which generates a pressure pulse to inject tiny droplets onto the surface of a balloon 16. A nozzle is moved in a fixed pattern over the surface of the balloon 16 to coat it uniformly with droplets. The liquid droplets are allowed to dry on the surface of the balloon 16 leaving behind a residual pattern of dots that, in total, contain the required quantity of therapeutic agent to meet the target concentration.

By selectively coating only a portion of the balloon 16 surface, larger volume droplets may be placed on the balloon 16 surface that then dry into a white powdery structure, which may be considered clinically desirable. Coating solution development has shown that thicker layers of coating may produce a more desirable coating structure. By placing small droplets in close proximity to one another, the uniformity of the coating from a clinical perspective is likely not compromised because the drug diffuses over short distances in a coronary artery. By having a pulse that injects the droplet onto the balloon 16, the need to provide precise containers for distribution of the coating solution may be eliminated. In addition, because the droplets are so small, complete drying of the coating generally occurs in minutes rather than hours.

One embodiment of the present disclosure involves the configuration of catheter balloon 16 folds 22 to optimize the application, distribution, containment, and drying of a coating solution to obtain a predetermined or metered concentration of a therapeutic agent within the folds 22. The desired results may be accomplished using commercially available folding equipment and a custom conditioning process. The outcome is folds 22 with a pre-determined volume and shape specific for every balloon 16 diameter required for the final device and specific coating composition. This allows for an exact volume of a coating solution to be administered to the folds 22. The solution is then optionally dried, sterilized and sent to the end user within the folds 22.

Historically, balloons 16 for catheters have been folded to lower their profile and facilitate entry into the vascular system for placement at the target site for revascularization. Thus, minimizing the overall folded diameter is a consideration in optimizing the folding process. However, for coated balloons 16 this dynamic is reversed because the folds 22 act as containers for the coating solution. Therefore, the containers should be large enough to hold a dilute coating solution to achieve the desired therapeutic concentration but small enough to distribute the coating uniformly.

Figure 4:
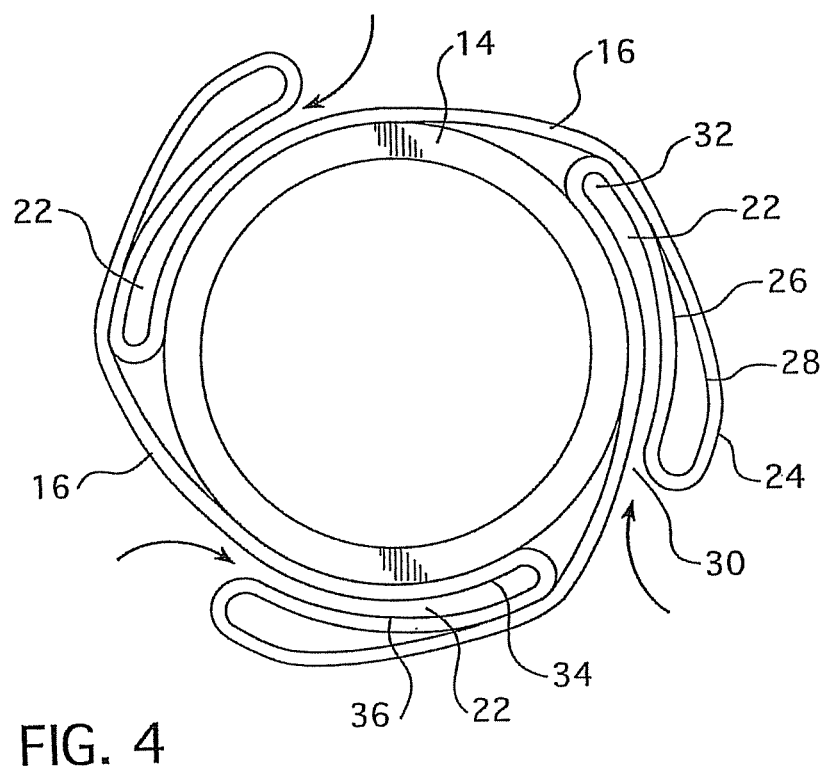
FIG. 4 is a cross-sectional view of a folded balloon.

A folded balloon 16 with three folds is shown in FIG. 4. As can be seen from the figure, a folded balloon 16 consists of pleats 24 that are pressed together and then wrapped substantially uniformly around the inner shaft 14 of the balloon catheter. A closed space is formed by the inner surface 26 of the pleat 24 to the outside surface 28 and the portion of the balloon 16 adjacent to the inner shaft 14. The fold 22 is characterized by a depth defined as the distance from the entrance 30 to the container to the fold 22 to its bottom 32, a width defined as the distance from the inside surface 34 of the fold 22 to its outside surface 36, and a length defined as the axial distance from the most distal point of the fold 22 to its most proximal point (not shown). Each of these dimensions can be modified by the balloon 16 folding process itself and optimized to maintain the concentration of the therapeutic agent during delivery to the treatment site.

Of the three dimensions, fold 22 depth may have the most impact on coating. Fold 22 depth considerations may be important for filling, retaining, distributing and drying the coating solution on the balloon 16. The ideal depth may be a trade off between a shallow depth, which allows for easy penetration and filling of the fold 22 with reduced ability to retain the fluid, against a deeper depth which is more difficult to fill but retains the coating solution more securely. This is a result of the interplay between the material, the surface tension, and viscosity of the solution. In general, higher surface tension and solution viscosity may make penetration of the folds 22 more difficult but allow for better retention. As a general rule, more concentrated coating solutions will have both higher surface tension and higher viscosity. In an example, a fold 22 depth of approximately 1.5 millimeters±50% may be, in one embodiment, an acceptable trade off between ease of filling and retention of coating solution.

A determinant in fold 22 depth is the number of folds 22 for a given balloon 16 size. More folds 22 result in shallower fold 22 depths. The standard folding process uses three folds 22 for all balloon 16 sizes. As can be seen in Table 1 the fold 22 depth varies from 0.16 mm for a 2.0 mm balloon 16 to 3.92 mm for a 10 mm balloon 16. This change in fold 22 depth has resulted in coating variability when using a dipping process. Smaller diameter balloons 16 are generally easier to fill while larger diameters are generally more difficult. During validation studies of the automated drip coating system, it was difficult to obtain adequate distribution of coating in the folds 22, especially on larger balloons 16. To eliminate this non-uniformity in coating distribution, the number of folds 22 is changed with each balloon 16 diameter and coating composition to better optimize the fold 22 depth. In an example, Table 1 shows the number of folds 22 for each balloon 16 diameter using a fold 22 depth of approximately 1.5 millimeters.

In conjunction with the fold 22 depth, the fold 22 width may be controlled to obtain the proper sized container to hold the volume of coating solution required to obtain the desired therapeutic concentration on the balloon 16. For example, in conjunction with the above fold 22 depths, a fold 22 width of approximately 0.11 mm±100% provides a fold 22 container that will allow enough solution with a higher concentration of therapeutic agent, for example a 150 mg/ml solution, to be applied to a balloon 16 in one application session. In this example, the fold 22 could be completely closed or have a fold 22 width of 0.22 mm, which would allow easier application and increased drug load.

TABLE 1

Fold Depths

| Shaft Dia | Balloon Dia (mm) | # Folds | Depth (mm) | # Folds | Depth (mm) |
|---|---|---|---|---|---|
| 4 Fr | 2.0 | 3 | 0.16 | 2 | 0.29 |
|  | 4.0 | 3 | 1.18 | 3 | 1.18 |
|  | 5.0 | 3 | 1.71 | 4 | 1.25 |
|  | 6.0 | 3 | 2.23 | 5 | 1.30 |
| 5 Fr | 4.0 | 3 | 1.00 | 3 | 1.00 |
|  | 5.0 | 3 | 1.52 | 3 | 1.52 |
|  | 6.0 | 3 | 2.05 | 4 | 1.51 |
|  | 7.0 | 3 | 2.55 | 5 | 1.49 |
|  | 8.0 | 3 | 3.07 | 6 | 1.48 |
| 6 Fr | 9.0 | 3 | 3.39 | 7 | 1.39 |
|  | 10.0 | 3 | 3.92 | 8 | 1.40 |

During the coating process, the exact amount of coating solution required for a given fold 22 may be determined. For example, Table 2 shows the volume of coating solution required for different configurations and different solution concentrations. The volume ranges from 21 microliters for a 2.0×20 mm balloon 16 up to 670 microliters for a 10.0×150 mm balloon 16 while using a low therapeutic concentration solution, for example a 30 mg/ml drug coating solution. The balloon 16 fold 22 for each balloon 16 size may then be tailored to match this fluid volume. This process involves developing the balloon 16 folding process to yield the depth and width that are required for the specific coating solution formulation being used. Alternatively, the concentration of coating solution can be varied to match the fold 22 volume.

TABLE 2

Solution Requirements

| Balloon Dia | 30 mg/ml Solution (μl) Balloon Length (mm) | | | 90 mg/ml Solution (μl) Balloon Length (mm) | | | 180 mg/ml Solution (μl) Balloon Length (mm) | | |
|---|---|---|---|---|---|---|---|---|---|
| (mm) | 20 | 80 | 150 | 20 | 80 | 150 | 20 | 80 | 150 |
| 2.0 | 21 | 71 | 130 | 7 | 24 | 43 | 4 | 14 | 26 |
| 3.0 | 34 | 110 | 198 | 11 | 37 | 66 | 7 | 22 | 40 |
| 4.0 | 40 | 141 | 258 | 13 | 47 | 86 | 8 | 28 | 52 |
| 5.0 | 52 | 178 | 325 | 17 | 59 | 108 | 10 | 36 | 65 |
| 6.0 | 65 | 266 | 392 | 22 | 89 | 131 | 13 | 53 | 78 |
| 7.0 | 79 | 314 | 460 | 26 | 105 | 153 | 16 | 63 | 92 |
| 8.0 | 94 | 295 | 529 | 31 | 98 | 176 | 19 | 59 | 106 |
| 9.0 | 109 | 336 | 599 | 36 | 112 | 200 | 22 | 67 | 120 |
| 10.0 | 126 | 377 | 670 | 42 | 126 | 223 | 25 | 75 | 134 |

The placement of coating solution only in the folds 22 of balloons 16 allows for the ability to place a protective sheath over the balloon 16 while the solution is still liquid without damaging or removing coating solution from the balloon 16. In addition, the placement of the protective sheath also provides a mechanism for maintaining the desired fold width that in turn may allow for uniform distribution along the length of the fold 22. Also, protection of the dry coating during subsequent steps of manufacturing and preparation for clinical usage may be achieved. The folds 22 act as a mechanical protector against abrasion during clinical preparation and also for introduction through an introducer and travel through the vascular system to the target revascularization site. This allows for delivery of a desired therapeutic concentration at the delivery site. For balloons 16 that have a significant percentage of the coating on the outside surfaces, the placement and removal of the protective sheath as well as the mechanical abrasion associated with entry through a vascular introducer affords an opportunity for loss of coating from the balloon 16 surfaces. Having the correct container size may allow for the exact amount of coating solution to be applied to the balloon 16 in one application session. Filling the container so that it is completely full may automatically distribute the coating solution within the balloon 16 folds 22 which, when the coating solution dries, may give a more uniform distribution of the residual solid material; thereby providing more uniform application of the therapeutic to the application site. Since the balloon 16 folds 22 are accurately sized and a metered amount of therapeutic coating solution is applied, the concentration of therapeutic is more consistent from balloon 16 to balloon 16.

The folding configurations described above and embodied in the present disclosure may be used with any application of a coating, including for example a therapeutic agent, onto a catheter balloon 16, such as, without limitation, metered or dip coated applications.

Figure 5:
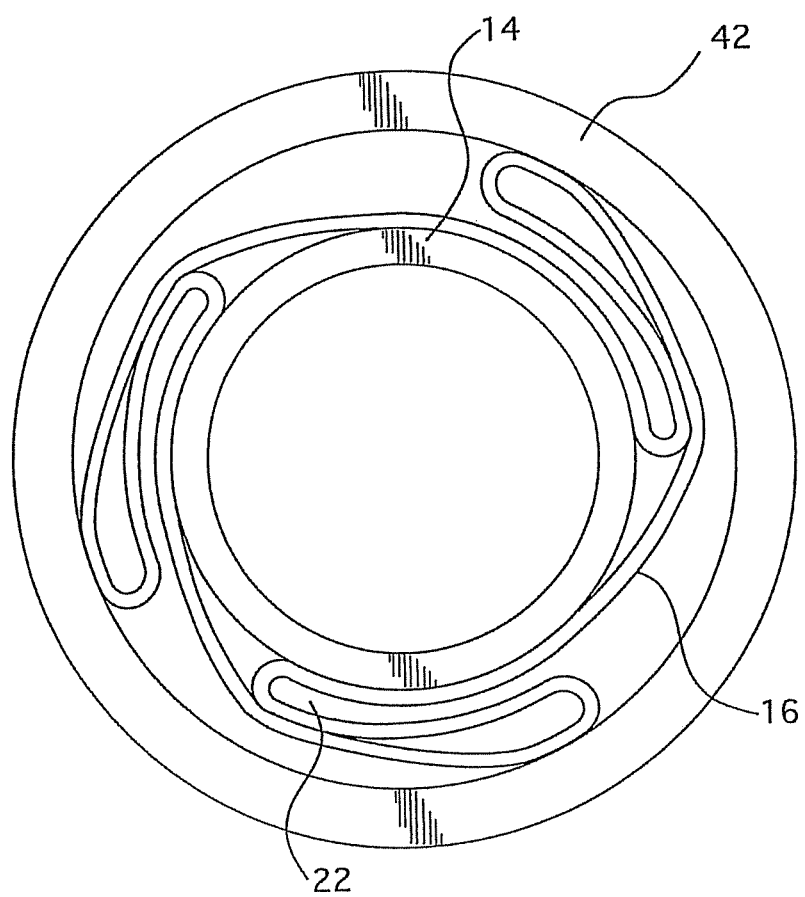
FIG. 5 is a cross-sectional view of a folded catheter balloon enclosed by a specifically-sized protective sheath.

A further embodiment of the present disclosure includes the use of a specifically-sized protective sheath 42 to distribute the coating, including for example a therapeutic agent, on a catheter balloon 16. The specifically-sized protective sheath 42 may be substantially specifically-sized for a given balloon 16 diameter. See FIG. 5. This embodiment may be easily applied and may be effective when used in conjunction with a metered application method, but can also be used with any application method, including for example the dip coating method for application of a therapeutic agent on a catheter balloon 16. For example, if a coating solution is only injected into the folds 22, the specifically-sized protective sheath 42 may be applied immediately after coating. If the coating solution is applied either partially or exclusively to the outside surfaces of the balloon 16, then a short air drying step may be necessary to allow the surface of the coating to harden to the point where placement of the specifically-sized protective sheath 42 does not abrade the coating from the balloon 16. Because external surfaces dry more rapidly than internal surfaces of the folds 22, placement of the specifically-sized protective sheath 42 may redistribute the liquid coating solution in the folds 22 more uniformly. Other techniques, such as plasma treating for example, may help facilitate this process.

Figure 6A:
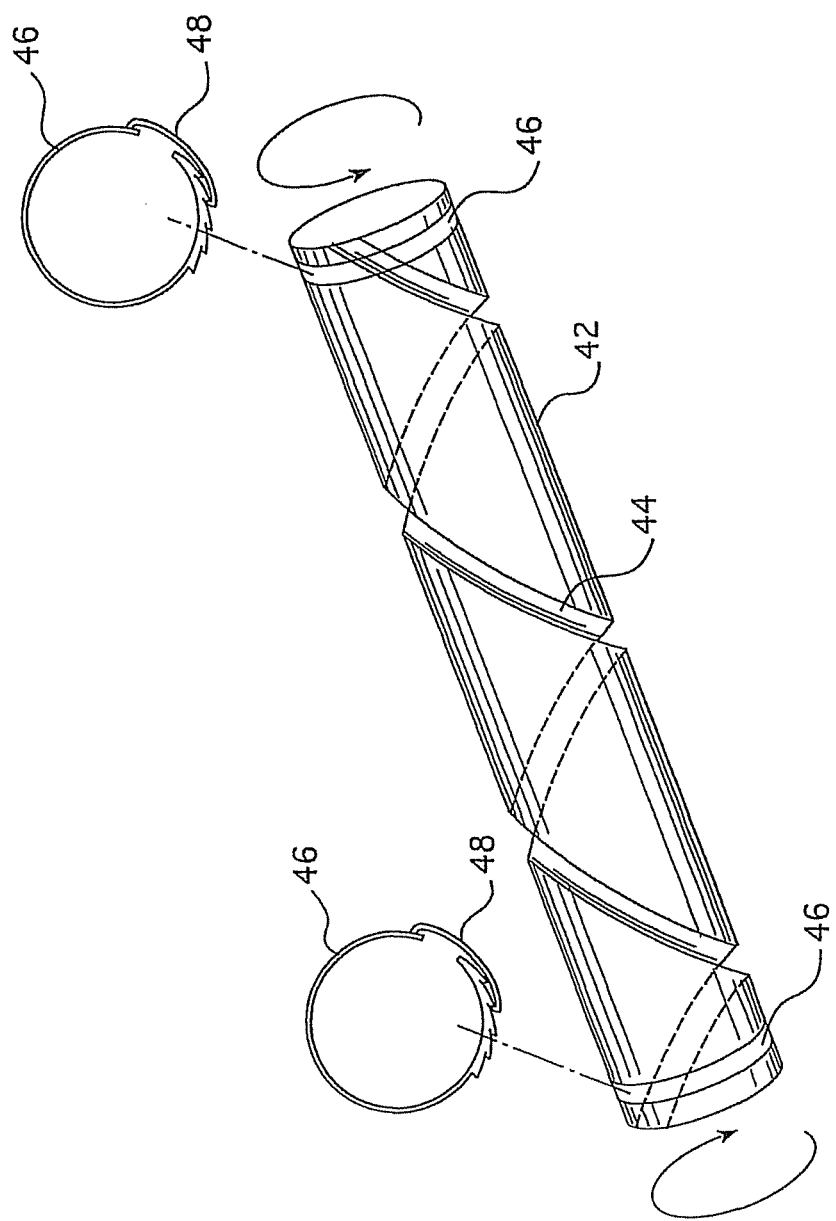
FIG. 6A and FIG. 6B depict a slotted protective sheath (FIG. 6A) and a non-slotted protective sheath (FIG. 6B) enclosing a catheter balloon using a ratcheting mechanism and securing with closing bands.
Figure 6B:
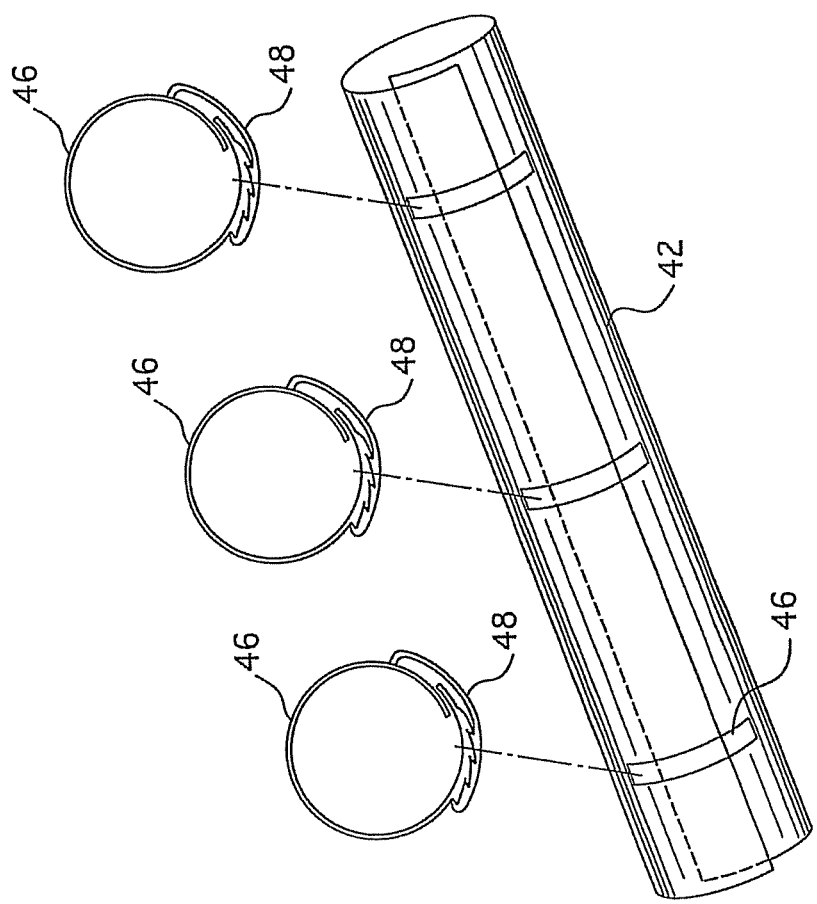

Optionally, the specifically-sized protective sheath 42 has spiral slits 44 around the circumference allowing for both uniform distribution and faster drying time. See FIG. 6A. FIG. 6B shows a non-slotted specifically-sized protective sheath 42. Once the balloon 16 (not shown) is in place, the ends of the specifically-sized protective sheath 42 are twisted with opposing force using a ratcheting mechanism to constrict the tubing, causing slight pressure on the balloon 16 surface. See FIG. 6A. The pressure may reduce relaxing of the balloon 16 during sterilization, shipping, and storage. The specifically-sized protective sheath 42 is held in place with at least one closing band 46 at each end using a hooking mechanism 48. The specifically-sized protective sheath 42 is installed over a drug coated balloon 16, minimizing the damage to the therapeutic coating. The therapeutic coatings are not damaged by installation and removal of the specifically-sized protective sheath 42. The specifically-sized protective sheath 42 also provides standard protection during processing and treatment. Furthermore, the specifically-sized protective sheath 42 is breathable, particularly with slits 44, allowing for drying of the coating while in a protected state.

Because the coating solution is in contact with the balloon 16 surface for a longer period of time, under the influence of the specifically-sized protective sheath 42 better adhesion may be obtained between the balloon 16 and the dried coating. The specifically-sized protective sheath 42 placed over the balloon 16 shortly after the application of the coating solution allows the balloons 16 to be handled sooner compared to a multiple dip process, thereby increasing production and decreasing costs. Because the coating solution is still liquid, the balloon 16 profile may be made smaller and more uniform to mitigate the effects of distortion caused by solvent interaction with the balloon 16 material.

In another embodiment, a specifically-sized protective sheath 42 is placed over the catheter balloon 16 first and then the coating applied inside the folds 22. For example, metered injection could be performed using a syringe, cannula, or tube covering the end of the device. The specifically-sized protective sheath 42 may be specifically-sized such that the folds are not completely closed. In an example, the specifically-sized protective sheath 42 has a diameter about 1-12 thousandths of an inch larger than the diameter of the balloon 16. In addition, the specifically-sized protective sheath 42 may be substantially sized to obtain a desired concentration of a therapeutic agent on the catheter balloon 16 with one application of a coating having a given composition and therapeutic agent. The coating is then forced into the specifically-sized protective sheath 42 and thus into all the folds 22. The volume necessary to fill the folds 22 may be calculated or visually determined. Drying may occur over time, for example within 24 hours in ambient air, or optionally in an oven at 50±20 degrees Celsius for 2-4 hours.

Figure 8:
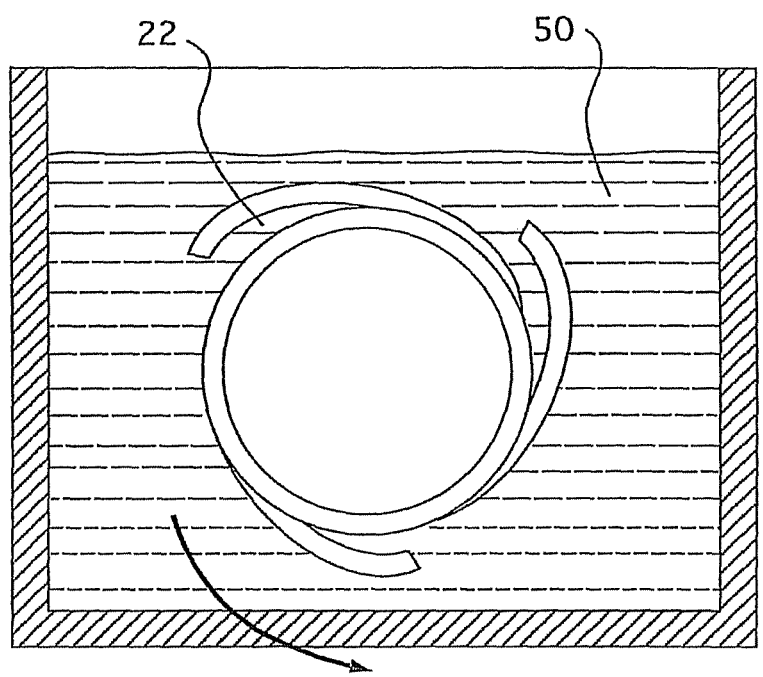
FIG. 8 is a cross-sectional view of a catheter balloon being coated by rotation in a coating solution in a direction that slightly opens the balloon folds while substantially simultaneously being pulled length-wise.

Other embodiments enhance the dipping process. A vacuum or a pressure or a combination thereof may be used to force the coating into the folds 22 either before or after the specifically-sized protective sheath 42 is placed over the balloon 16, i.e. pressurized dip coating. For example, a balloon catheter is placed into a coating solution 50 in a pressure chamber 52, a pressure is applied forcing the coating into the folds 22 of the balloon 16, and after the pressure is removed the catheters are removed to dry. See FIG. 7A and FIG. 7B. In an alternate method, the balloon 16 is rotated in the coating solution 50 in a direction that causes the folds 22 to open slightly for coating deeper into the folds 22. See FIG. 8. Optionally, the balloon 16 is pulled through the coating solution 50 length-wise as it is rotated to provide a more uniform coating. Also, optionally, the balloon 16 is slightly inflated prior to placing in the coating solution 50 to maximize and to improve the uniformity of the coating. These embodiments in particular, alone or in combination, may enhance the dipping method to a single step.

Figure 9:
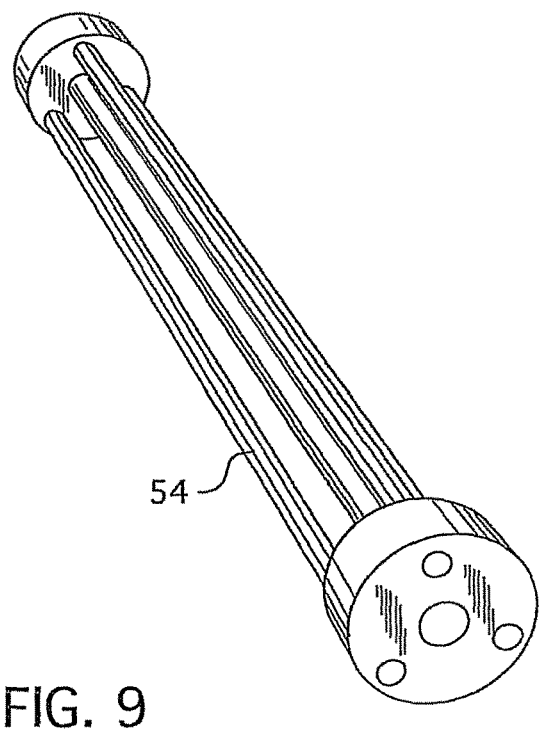
FIG. 9 is a schematic diagram of aluminum rod spacers used to hold the folds of a catheter balloon open during coating.

A further embodiment for applying the coating inside the folds 22 comprises the use of at least one spacer 54 or a wick 56 to draw a coating solution 50 into at least one fold 22. See FIG. 9 and FIG. 10. The spacers 54 may be any hard, inert material, for example plastics such as Teflon® or Delran® or metal such as aluminum, which opens the folds at least partially. In an example, the spacers 54 are aluminum rods. See FIG. 9. The spacers 54 are positioned at the proximal and/or distal end of the balloon 16 and placed into the folds 22 during the folding process or after the balloon 16 is folded with or without a protective sheath. In one embodiment, the spacers 54 are substantially long enough to hold the folds 22 at least partially open and may be the length of the balloon 16. The width of the spacers 54 is wide enough to hold the folds 22 at least partially open and may be as wide as the width of the fold 22. In an example for a 4.0×20 mm balloon, the spacers may be 1.1 mm wide and 20 mm long. Spacers 54 may be used with any coating application method, including with methods that require the folds 22 to be slightly open, such as the dipping method. After coating, the spacers 54 may be removed by hand or by a mechanical means. If using a method requiring a bath, the spacers 54 may be removed in the bath. In the example of aluminum rod spacers 54 inside the folds used with the dipping method, the spacers 54 may be slipped out of the folds 22 during or directly after dipping, thus allowing the coating solution to fill the void, but may be left in place long enough to hold the folds 22 open.

Figure 10:
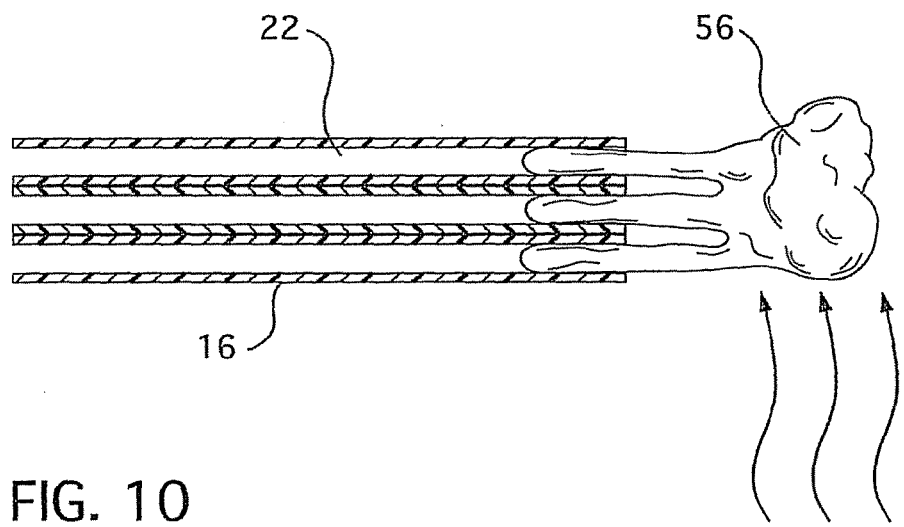
FIG. 10 is a cross-sectional view of a catheter balloon with a wick inserted into the folds of the balloon for drawing a coating solution into the folds.

The wick 56 may be, for example and without limitation, any plastic-based rope-like substance, a nylon material, a cotton material, an organic material, any synthetic materials, or a combination thereof. The wick 56 may be placed into the folds 22 during folding on the distal end of the balloon 16. See FIG. 10. Wicks 56 may be used with any coating application. The wick 56 draws the coating solution into the folds 22 by capillary action, so that the folds 22 are filled. The wick 56 may be removed either in a bath solution if one is used or out of a bath solution and either by hand or by mechanical means. The wick 56 is optionally removed after coating but before air-drying, or as an alternative the wick is left in to promote faster drying as air is blown across (FIG. 10). Use of spacers 54 or a wick 56 promotes metered application of a specific amount of coating, such as a therapeutic agent.

Another embodiment for applying the coating inside the folds 22 pertains to a balloon 16 conditioning process whereby the balloon 16 partially opens when submersed in a bath of at least one solvent, such as, for example and without limitation, ethanol, methanol, isopropanol, acetone, diethyl ether, diisopropyl ether, and chloroform before application of the coating. The opening of the balloon folds 22 may also be promoted by using one or more of such solvents in the formulation of coating solution. In an alternate embodiment, the solvent(s) may be sprayed on to partially open the folds 22. The solvent(s) may be applied in one step or multiple steps. In an example of a two-step process, the balloon 16 is first dipped into one solvent, such as acetone, and subsequently dipped into a second solvent, such as ethanol. The therapeutic coating may be applied by any method. If desired, the balloon 16 may be refolded after coating by the application of the specifically-sized protective sheath 42.

Figure 11:
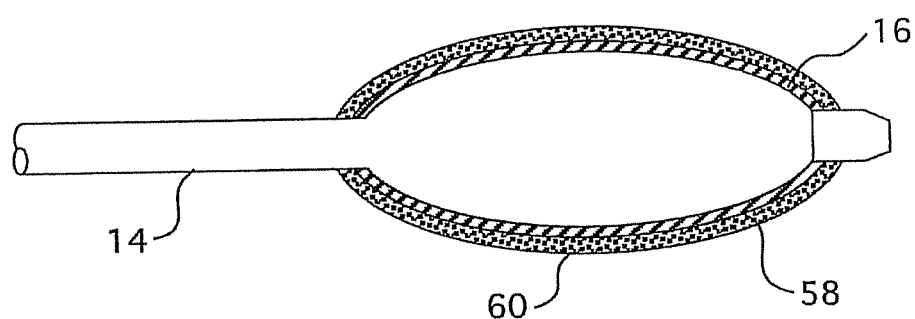
FIG. 11 is a schematic diagram of a catheter balloon with an intermediate layer between the balloon and a coating.

Additional embodiments of the present disclosure pertain to techniques for allowing optimization of balloon 16 performance, coating structure, and coating adherence independently by providing an intermediate material layer 58 on the balloon 16 to act as a bridge between the balloon 16 and therapeutic coating 60. See FIG. 11. The intermediate layer 58 adheres to the balloon 16 material on one side and provides for adherence of the therapeutic coating 60 on the other side. This may be useful for hydrophilic drugs, such as Doxorubicin, and others that have a tendency to be lost during the balloon 16 insertion process. Other examples of hydrophilic drugs include, without limitation, caffeine, nicotine, netilmicin, dopamine, sugar, sugar alcohols, other organic neutral substances, lipophilic amino acids, salts of organic and anorganic acids and bases, contrast mediums or dyes commonly used in medicine, coagulation inhibitors such as heparin, platelet aggregation inhibitors such as acetylsalicylic acid, and salicylic acid. Balloon 16 performance characteristics such as compliance and burst strength may be optimized independently from therapeutic coating 60 characteristics such as structure and adherence.

Several different methods may be used to obtain the intermediate layer 58. In an example, a thin, second layer of material is extruded onto the balloon 16 tubing before the balloon 16 is formed. In another example, the two materials are extruded independently and are adhesively bonded together after balloon 16 forming but before folding and heat setting. In another example, material is evaporated and deposited onto the balloon 16 surface via an electronic excitation process. This process may allow for plasma deposition to be controlled by choice parameters. Examples of materials that may require such treatment include without limitation Teflons, Polyethylene terephthalate (PET), Urethanes, and Polypropylene (PP). In an example, a Pebax Nylon is deposited as a thin layer over a PET based balloon 16 resulting in a stiff solid balloon 16 with substantially similar release characteristics as the standard balloons 16. Another example is to plasma treat the balloon 16 surface before or after folding with a nonpolymer forming plasma. In this technique, the balloon 16 surface is activated via formation of new functional groups or creation of micro roughness on the surface, which may aid adhesion of the therapeutic coating 60 to the balloon 16 surface.

A balloon 16 material may be chosen to meet performance criteria such as burst pressure and compliance and the therapeutic coating 60 may be designed to meet compositional and morphological criteria. As a result, therapeutic coating 60 adherence to a balloon 16 surface is a by-product of the optimization of balloon 16 material and therapeutic coating 60 characteristics. However, adherence may be clinically important for delivery of the therapeutic to the target site for revascularization. From a design perspective, it may be desirable to optimize balloon 16 performance, therapeutic coating 60 structure, and therapeutic coating 60 adherence independently. As an example, if the current balloon 16 material were changed, development of a new therapeutic coating 60 may be required to maintain the same clinical effectiveness of the therapeutic coating 60 as with the current material. This embodiment allows balloons 16 with much different structural properties than current balloons 16, i.e., balloons which are more compliant but have the same burst pressure, to be tailored to match that of the current material by the addition of an intermediate layer 58. The intermediate layer 58 may allow the use of the therapeutic coating 60 and process for applying a therapeutic coating 60 to the balloon 16 providing an improved delivery platform, such as better release characteristics, and a clinically more effective therapeutic coating 60.

Further embodiments comprise the addition of a priming layer to the catheter balloon 16 to increase drug adherence or enhance device properties. Examples of priming layers include, without limitation, iopromide or radiopaque materials, adhesive, hydrogel, polymeric materials, biodegradable layers, biocompatible layers, hydrophilic materials, lubricious materials, epoxies, etc. In an example, the catheter balloon 16 is first coated with iopromide, then coated with the therapeutic agent, and finally coated with a second layer of iopromide. In another example, the catheter balloon 16 is first coated with a hydrogel or adhesive and then coated with the therapeutic agent. In an alternative example, the therapeutic agent is mixed with the hydrogel or adhesive before coating. In another example, the therapeutic agent is mixed with iopromide or Ultravist® contrast media.

In one embodiment, a catheter balloon 16 is coated with a soluble film 62 comprising a therapeutic agent, such as paclitaxel. See FIG. 12. Example materials used to make the soluble film 62 include, without limitation, porcine, bovine, aquatic vertebra (fish), avian, and Ovo based gelatin, such as pork skin derivatives and Gelfoam, gelatinized starch, cellulose, fruit/vegetable base, for example cooked apples or agar, and any other organic polymer. In an example, the materials are in powdered form and mixed with water or other solvents to produce the soluble film 62. In another example, the solution is mixed with 30 mg/ml of Paclitaxel, 100 ml of purified water, 2 ml of Ultravist® contrast media and 0.25 oz of gelatin. The solution is placed into molds in which the base solidifies and forms the strips or tubes, which are inserted into the folds 22 or applied over the folded balloon 16. The dimensions of the strips may have a thickness of about 0.05 mm to about 1 mm, width of about 0.05 mm to about 4 mm and a length that covers the length of the balloon 16 intended to coat. The dimensions of the tubes may have a thickness of about 0.05 mm to about 1 mm, a diameter of about 1 mm to about 1 cm, and a length that covers the length of the balloon 16. The amounts shown above may be adjusted using more or less paclitaxel, more or less Ultravist® contrast media or more or less gelatin. In yet another example, fruit and/or vegetables are reduced down to produce a thick puree base. The base containing 100 ml of reduction may be mixed with 50 mg/ml of Paclitaxel and 3 ml of Ultravist® contrast media, which is placed in molds for strips or tubes. The molds may be dried in an oven at 140 degrees F. for 3-12 hours and/or a dehydrator. The soluble film 62 may then be applied to the balloon 16. In an alternate embodiment, the balloon 16 is dipped into the base before drying. The balloon 16 may be dried and have a soluble film 62 over the surface. In another embodiment, the base is sprayed on the balloon 16.

Figure 12A:
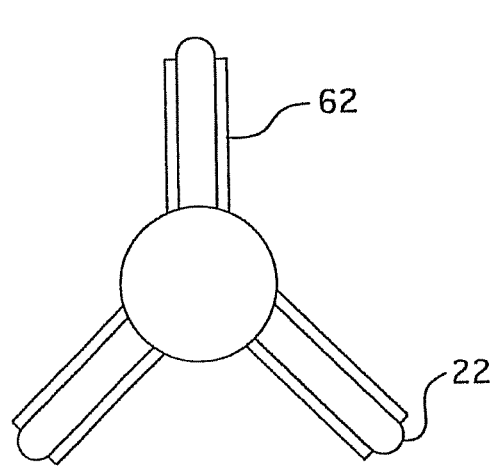
FIG. 12A-FIG. 12I are schematic diagrams of a catheter balloon coated with a soluble film with FIG. 12A and FIG. 12B depicting soluble film applied post pleating prior to folding of the balloon, FIG. 12C depicting soluble film applied post folding of the balloon in the folds, FIG. 12D depicting soluble film applied around the outside, FIG. 12E depicting a combination, and FIG. 12F through FIG. 12I depicting soluble film applied in various configurations prior to pleating and folding the balloon.
Figure 12B:
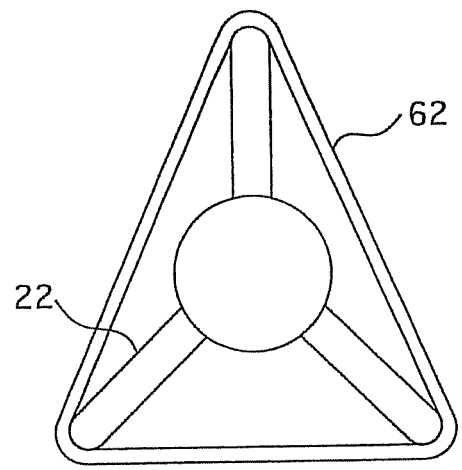
Figure 12C:
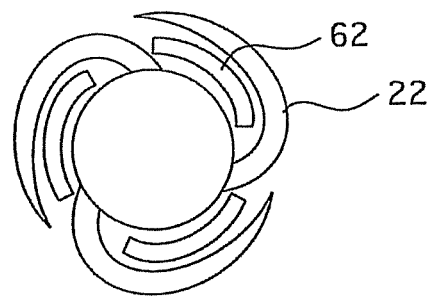
Figure 12D:
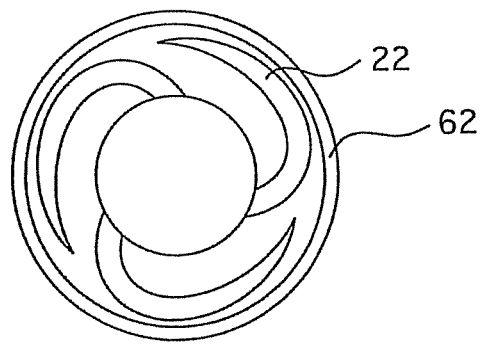
Figure 12E:
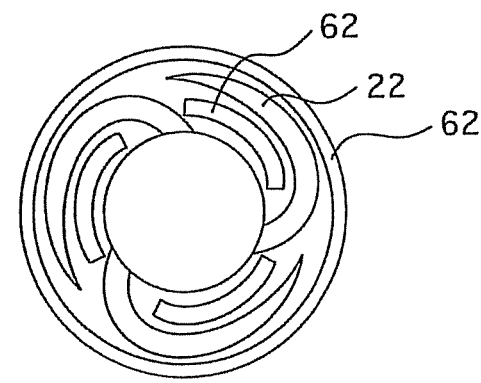
Figure 12F:
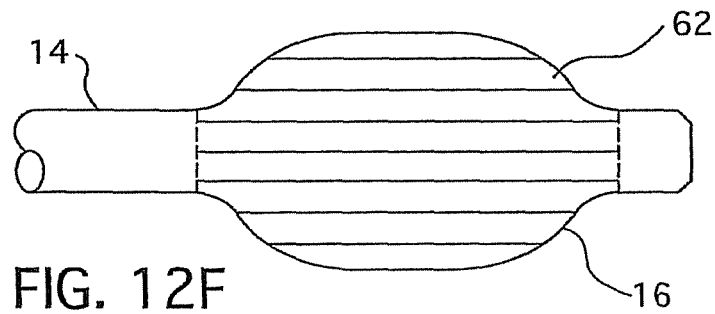
Figure 12G:
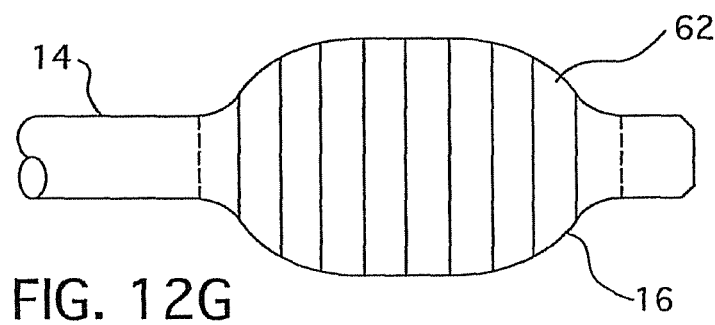
Figure 12H:
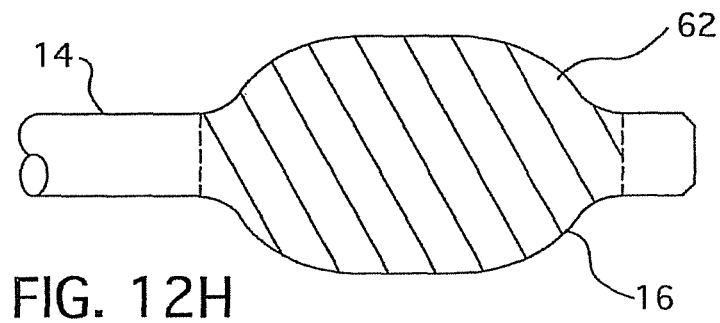
Figure 12I:
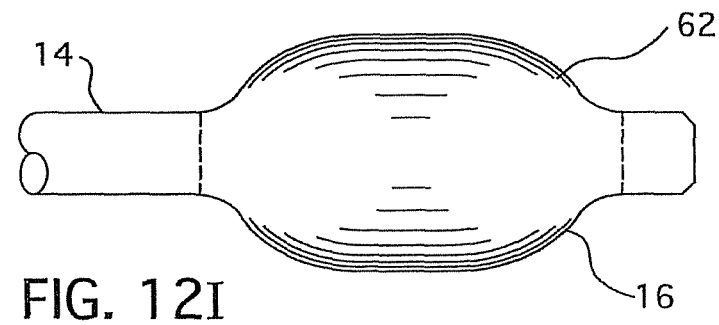

The soluble film 62 may be applied over the formed balloon 16 and/or folded along with the balloon 16. The soluble film 62 may be applied post pleating prior to folding. See FIG. 12A and FIG. 12B. The soluble film 62 may be applied in the folds 22 (FIG. 12C), over the folded balloon 16 (FIG. 12D), or a combination (FIG. 12E) before the optional protective sheath. The soluble film 62 may be in the form of strips wrapped around the balloon 16 vertically or axially (FIG. 12F-FIG. 12H) or can coat the entire balloon 16 (FIG. 12I). The strips of soluble film 62 may be in at least one fold of the folded catheter balloon 16. The strips may be placed in at least one fold 22 of the catheter balloon 16 by sliding the strips between the folds 22 or in an alternative example the soluble film 62 strips may be folded into the folds 22 during the folding process, for example through placement of soluble film 62 strips on the folding heads. In another example, soluble film is applied during the extrusion process of the base balloon 16 material. As the extrusion media (tubing) exits the extruder a separate process step may be in place where the soluble film 62 tube is slid over the nylon or other material balloon 16 tubing. Alternatively, the soluble film 62 may be applied by any combination of methods.

In one embodiment, the thickness of the soluble film 62 is within the folding range such that the overall catheter profile does not increase. The soluble film 62 may be wetted by the user prior to use or the blood in the vessel may be sufficient to dissolve the soluble film 62 at the target location. The soluble film 62 may attach to the vessel wall and dissolve over time or may remain attached to the catheter and leach the therapeutic agent out at the target location. In an example using Paclitaxel and Ultravist® contrast media, the Ultravist® contrast media acts as the carrier or excipient to allow for the Paclitaxel uptake into the vessel wall. The time frame may at a minimum about 30 sec to 2-3 min. In this example, since the soluble film 62 could be sticky, it may be deposited against the wall like a gel or thick film. Depending on the thickness of the soluble film 62, it could dissolve over 30 sec up to 24 hours. In another example, the soluble film 62 remains in place for months as the soluble film 62 becomes part of the vessel with therapeutic release over 30 days, similar to a stent. By way of any of these variations or combinations thereof, the metered concentration of the therapeutic agent remains consistently within the dosing range.

Embodiments of the present disclosure provide the combined ability to control both the amount of therapeutic agent and its distribution on a folded catheter balloon 16 or other medical device. The ability to control these two aspects of a coating is non-existent in the current dipping process. In an example, a target therapeutic concentration can be placed on the balloon 16 within 0.1 micrograms per square millimeter. As a result, only the required amount of therapeutic necessary to achieve the desired therapeutic effect is applied to the balloon 16. This optimizes the treatment process for the patient. The control of therapeutic location allows for optimization of therapeutic distribution to obtain the desired clinical effect while also maximizing the ability to deliver the therapeutic to the target site for revascularization. By placing more therapeutic in the folds 22 of a catheter balloon 16, a natural protection is afforded for, for example, the loss of the dried coating from abrasion during manufacturing, clinical preparation and introduction of the catheter into the vascular system through a homeostasis valve introducer. In another example, by reducing the application process to a single injection, manufacturing times can be reduced and the amount of toxic waste and its handling can be minimized, all of which reduces manufacturing costs. These methods can use any solution chemistry with only minor modification to the application system. These features may provide a high degree of flexibility to tailor the solution chemistry to enhance the effectiveness of the dried coating.

Examples

Metered Injection

The following discussion illustrates non-limiting examples of embodiments of the present disclosure. Techniques for metering an exact volume of coating solution onto catheter balloons can use, for example, precision glass syringes, such as those manufactured by Hamilton Company. The syringe consists of a glass barrel with a precision bore, mating plunger with an accurately machined Teflon® seal and a distal fluid connector with either a luer taper, fixed needle or removable needle. The Hamilton Series 700 syringes are available in volumes ranging from 5 to 500 μl and the Series 1000 syringes ranging from 1 to 100 ml.

To hold and rotate the balloon, a custom mounting fixture was designed containing the following elements:

Touhy Borst Gasket to hold the shaft of the balloon catheter near the proximal balloon bond;

Guidewire Holder to support the distal end of the guidewire used to stiffen the balloon section of the catheter;

Catheter Drive Pulley to interface with the motor to rotate the balloon;

DC Motor to rotate the balloon;

Motor Drive Pulley and Belt to interface with the Catheter Drive Pulley and rotate the balloon at 60 rpm.

This fixture was designed for use in conjunction with a stereomicroscope.

A metering system may be a manual syringe application method to dispense coating solution onto a balloon. This method requires refilling of a syringe after every application of solution. Additionally, the refilling process exposes coating solution to air, causing evaporation of lower boiling point solvents and subsequent destabilization of the coating solution. To enhance accuracy and promote solution stability, an application system was developed using a syringe pump, precision syringe, three-way valve and a solution reservoir. This system enhanced the metering process by using a syringe pump that can repeatedly move the plunger a fixed distance to precisely dispense a predetermined volume of solution onto the balloon. At the center of the system is a microliter dispensing pump that uses a Hamilton precision glass syringe as described above. The distal end of the precision syringe interfaces with a three-way valve that can select a fluid reservoir for refilling or fluid tubing for delivery of solution. At the other end, the plunger interfaces with a sliding mechanism on the syringe pump which is used to push the plunger an accurate distance during dispensing. Using a custom-designed linear screw driven by a stepper motor and a precision glass syringe, solution injection volume variability was reduced to less than ±5 percent.

Approximately 30 catheters of different balloon dimensions and solution compositions were made for testing in a first study. For each lot of catheters, high performance liquid chromatography (HPLC) testing was done on 5 balloons with stents and 5 balloons without stents to determine the concentration of paclitaxel and iopromide on each balloon. The testing was done using the same protocols used historically on dip coated balloons. The results are summarized in Tables 3 and 4.

TABLE 3

Preclinical Study Paclitaxel Concentration

| | Paclitaxel (ug/mm$^2$) Without Stent | | | | Paclitaxel (ug/mm$^2$) With Stent | | | | |
|---|---|---|---|---|---|---|---|---|---|
| | Avg | Min | Max | Var | Avg | Min | Max | Var | Loss |
| 3.5 × 20 | | | | | | | | | |
| Exp 4 | 4.52 | 4.23 | 4.78 | 6.1% | 4.31 | 3.85 | 4.61 | 8.8% | 5% |
| Exp 3 | 4.54 | 4.39 | 4.70 | 3.4% | 4.43 | 4.38 | 4.45 | 0.8% | 3% |
| Exp 2 | 4.54 | 4.34 | 4.77 | 4.7% | 4.21 | 3.99 | 4.65 | 7.8% | 7% |
| Exp 1 | 5.11 | 4.64 | 5.41 | 7.5% | 4.69 | 4.43 | 4.91 | 5.1% | 8% |
| Control | 2.24 | 1.59 | 2.90 | 29.2% | — | — | — | — | — |
| 3.0 × 20 | | | | | | | | | |
| Exp 4 | 4.69 | 4.60 | 4.77 | 1.8% | 4.52 | 4.12 | 4.76 | 7.1% | 4% |
| Exp 3 | 4.74 | 4.71 | 4.79 | 0.8% | 4.60 | 4.47 | 4.70 | 2.5% | 3% |
| Exp 2 | 4.87 | 4.77 | 5.10 | 3.4% | 4.26 | 3.60 | 4.53 | 10.9% | 12% |
| Exp 1 | 6.40 | 6.05 | 7.01 | 7.5% | 5.36 | 4.39 | 5.89 | 14.0% | 16% |
| Control | 2.18 | 1.68 | 2.52 | 19.3% | — | — | — | — | — |

TABLE 4

Pre-clinical Study P/I Ratio

| | P/I Ratio Without Stent | | | | P/I Ratio With Stent | | | |
|---|---|---|---|---|---|---|---|---|
| | Avg | Min | Max | Var | Avg | Min | Max | Var |
| 3.5 × 20 | | | | | | | | |
| Exp 4 | 1.68 | 1.63 | 1.79 | 4.7% | 1.68 | 1.64 | 1.76 | 3.4% |
| Exp 3 | 1.65 | 1.64 | 1.65 | 0.3% | 1.68 | 1.66 | 1.69 | 0.7% |
| Exp 2 | 1.62 | 1.57 | 1.64 | 2.2% | 1.62 | 1.61 | 1.64 | 0.7% |
| Exp 1 | 1.69 | 1.64 | 1.70 | 1.6% | 1.69 | 1.64 | 1.78 | 4.1% |
| 3.0 × 20 | | | | | | | | |
| Exp 4 | 1.64 | 1.62 | 1.65 | 0.9% | 1.64 | 1.61 | 1.65 | 1.4% |
| Exp 3 | 1.66 | 1.62 | 1.65 | 0.9% | 1.67 | 1.67 | 1.70 | 1.1% |
| Exp 2 | 1.63 | 1.61 | 1.64 | 0.7% | 1.64 | 1.61 | 1.68 | 2.0% |
| Exp 1 | 1.70 | 1.68 | 1.68 | 0.2% | 1.74 | 1.66 | 1.80 | 4.2% |

Excluding the control, the results for unstented balloons show an increase in drug content and reduced intralot variability compared to dip coating. Pooling results for experiments 1 thru 4 and both balloon sizes gives an average paclitaxel content of 4.6 µg/mm$^2$ with a variation of ±9.4% compared to 2.2 µg/mm$^2$ with a variation of ±30%. The P/I ratio, which is the ration between paclitaxel and iopromide on the balloon, averaged 1.65 with a variation off 6.6%. The P/I ratio for dip coating was 2.0 with variation of ±25% so the averages are not comparable. These examples were made as six mixings of three different coating solutions over three days; thus demonstrating the repeatability of the process.

For stented balloons, the average paclitaxel concentration was 4.4 µg/mm$^2$ with a slightly higher variation of ±13.5%. This represents a drug loss of approximately 5.7%. The P/I ratio was unchanged between stented and unstented balloons.

A coating specification study corresponding to the above study was also done. For this study, rapid exchange PTCA catheters with 3.5×20 mm and 3.0×20 mm balloons were coated with two solutions. The total solution volume applied to the balloons was determined using 5 µg/mm$^2$ drug concentration which provided a margin of safety above the minimum acceptable value of 2.0 µg/mm$^2$. Solutions were injected into the folds and applied to the balloon surface using the syringe pump technique described above. Table 5 gives the solution specifications for each balloon diameter and solution configuration. For configuration 1, approximately two-thirds of the solution was placed in the folds and one-third on the outer surface. For configuration 2, the solution was placed only in the folds with some solution reaching the outer surfaces naturally.

A total of 60 catheters with 3.5×20 mm balloons and 40 catheters with 3.0×20 mm balloons were coated. After the coating dried, stents were crimped onto the coated balloons and the catheters were processed through final assembly, packaging and sterilization using standard manufacturing procedures. At the completion of manufacturing, chemical analysis was done on both unstented and stented balloons.

TABLE 5

Coating Specifications

| | TOTAL SOLUTION (μL) | PER FOLD (μL) | OUTSIDE (μL) | OUTSIDE APPLICATIONS |
|---|---|---|---|---|
| 3.5 × 20 MM-30 UNITS | | | | |
| Configuration 2 | 10.5 | 3.5 | NA | NA |
| Configuration 1 | 17.5 | 4.0 | 5.5 | 1 |
| 3.0 × 20 MM-20 UNITS | | | | |
| Configuration 2 | 8.4 | 2.8 | NA | NA |
| Configuration 1 | 14.0 | 3.0 | 5.0 | 1 |

During coating, the feasibility of two concepts of a semi-automated coating system was confirmed: air-free exchange process for mechanically refilling the glass syringe and use of a precision screw coupled to a stepper motor to precisely move the plunger of a glass syringe.

In the first study, solution instability was encountered which was attributed to the constant exposure of solution to air during manual refill of the metering syringe after each fold. During the coating specifications study, a closed loop system was used with a larger plastic syringe acting as a reservoir for filling the smaller glass syringe. The only contact with air was the initial filling of both syringes. Subsequent fillings were done via a 3-way valve and withdrawal from the reservoir. No visible precipitation or coating segregation was observed during coating.

During the coating specifications study, glass slides were made after each group of five balloons. 45 μl drops of solution were metered onto the slide and the net weight gain measured after the solution dried. A total of 13 slides for each configuration were completed and the results shown in Table 6.

TABLE 6

Configuration Variability Analysis

| CONFIG-URATION | WEIGHT (μg) THEORY | WEIGHT (μg) AVG | ACCU-RACY | WEIGHT (μg) MIN | WEIGHT (μg) MAX | RANGE |
|---|---|---|---|---|---|---|
| Configuration 1 | 6.6 | 6.8 | 2.9% | 6.7 | 7.1 | ±2.7% |
| Configuration 2 | 10.9 | 11.1 | 1.4% | 10.7 | 11.5 | ±3.5% |

The results indicate a mixing error of less than 3% and repeatability over two hours and 60 balloons of ±3.5%. If the accuracy and repeatability are combined, the cumulative accuracy is ±5% which is within the target tolerance of 25.0% for the entire coating process.

Figure 13:
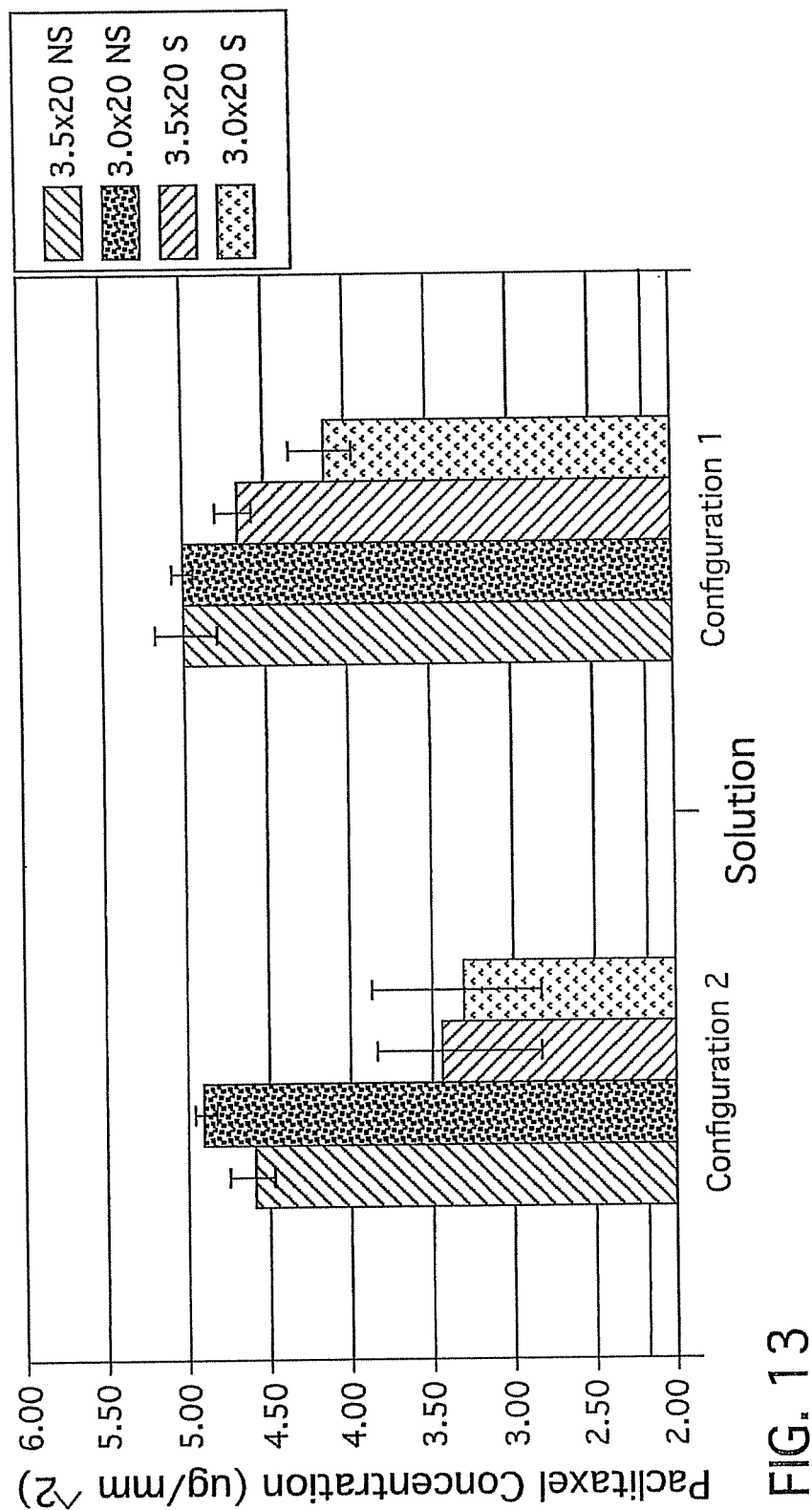
FIG. 13 is a graph depicting efficacy results from a coating specification study.

For each lot of catheters, high pressure liquid chromatography (HPLC) was performed on 5 balloons with stents and 5 balloons without stents to determine the concentration of paclitaxel and iopromide on each balloon. Testing was performed using the same protocols as the dip coated balloons. The results are summarized in Tables 7 and 8 and shown graphically in FIG. 13.

TABLE 7

Coating Specification Study-Paclitaxel Concentration

| | PACLITAXEL (μg/MM$^2$) WITHOUT STENT | | | | PACLITAXEL (μg/MM$^2$) WITH STENT | | | | |
|---|---|---|---|---|---|---|---|---|---|
| | Avg | Min | Max | Var | Avg | Min | Max | Var | LOSS |
| 3.5 × 20 | | | | | | | | | |
| Configuration 2 | 4.60 | 4.48 | 4.73 | 2.7% | 3.45 | 2.81 | 3.83 | 14.8% | 25% |
| Configuration 1 | 4.97 | 4.78 | 5.13 | 3.5% | 4.64 | 4.53 | 4.76 | 2.5% | 7% |
| 3.0 × 20 | | | | | | | | | |
| Configuration 2 | 4.88 | 4.82 | 4.94 | 1.2% | 3.31 | 2.82 | 3.87 | 15.9% | 32% |
| Configuration 1 | 4.96 | 4.89 | 5.03 | 1.4% | 4.11 | 3.94 | 4.28 | 4.1% | 17% |

TABLE 8

Coating Specification Study-P/I Ratio

| | P/I RATIO WITHOUT STENT | | | | P/I RATIO WITH STENT | | | |
|---|---|---|---|---|---|---|---|---|
| | Avg | Min | Max | Var | Avg | Min | Max | Var |
| 3.5 × 20 | | | | | | | | |
| Configuration 2 | 1.67 | 1.66 | 1.68 | 0.5% | 1.61 | 1.57 | 1.65 | 2.5% |
| Configuration 1 | 1.62 | 1.60 | 1.64 | 1.1% | 1.62 | 1.60 | 1.63 | 1.2% |
| 3.0 × 20 | | | | | | | | |
| Configuration 2 | 1.67 | 1.63 | 1.68 | 1.6% | 1.65 | 1.60 | 1.71 | 3.4% |
| Configuration 1 | 1.63 | 1.61 | 1.67 | 2.0% | 1.58 | 1.55 | 1.64 | 3.0% |

The results for unstented balloons show an increase in drug content and reduced intralot variability compared to dip coated balloons and somewhat better than the first set of experiments. The pooled results for both diameters and solution configurations gave an average paclitaxel content of 4.9 μg/mm$^2$ with a variation of ±6.2% compared to 4.6 μg/mm$^2$ with a variation of ±9.6% for first set of experiments balloons and 2.2 μg/mm$^2$ with a variation of ±30% for dip coated balloons. The P/I ratio averaged 1.65 with a variation of ±2.4% compared to the same value but a variation of 6.6% for the first set of experiments.

For stented balloons, the pooled paclitaxel concentration was 3.88 μg/mm$^2$ with a variation of ±25.2%. This represents an average drug loss of approximately 20%, higher than the first study. This change is essentially in Configuration 2 data. If only Configuration 1 data are included, then the numbers are 4.38 μg/mm$^2$ with a variation of ±6.0% which represents a loss of 11.6% from stenting.

As shown, results were similar for both studies. Similar results were obtained from studies performed using a different balloon composed of different materials, thus indicating the metered injection method is useful for various balloon materials and types.

Spacers

Hard, inert spacers may be used to enhance coating of the folds of a catheter balloon. In an example, Delrin® spacers having a width of 0.11 mm were used. The spacers were inserted at the distal end of the catheter balloon folds during the folding process. The balloon catheters were subsequently dip coated with a single dip in a standard paclitaxel coating solution bath. After drying, HPLC analysis was performed to determine the drug concentration on the devices. The goal of this study was to have a mean paclitaxel value of 1.5 ug/mm$^2$ and a P/I ratio of 2.0.

TABLE 9

Spacer Study Results

|  | Paclitaxel [μg/piece] | Iopromid [μg/piece] | Paclitaxel/Iopromid |
| --- | --- | --- | --- |
| Mean Value | 1.57 | .793 | 1.99 |
| Standard Deviation | 10.89 | 9.25 | 0.09 |

The results, as summarized in Table 9, indicate a mean value of 1.57 ug/mm$^2$ of paclitaxel and an overall P/I ratio of 1.99. These results demonstrate that the use of spacers provides a means to maintain fold width to enhance coating and produce desired coating results, including drug concentration. In addition, the use of spacers can decrease manufacturing time and costs by decreasing the number of dips required by the dip coating method to a single dip.

The present disclosure has been described with reference to specific details of particular embodiments thereof. It is not intended that such details be regarded as limitations upon the scope of the disclosure except insofar as and to the extent that they are included in the accompanying claims.

What is claimed is:

1. A method of coating an inside of at least one fold of a folded catheter balloon with a therapeutic agent, said method comprising placing a spacer inside at least one fold at a proximal or at a distal end of said catheter balloon, wherein said spacer holds said fold at least partially open.

2. The method of claim 1, wherein said placing of said spacer into said fold is substantially simultaneous with folding of said catheter balloon or after said catheter balloon is folded.

3. The method of claim 1, wherein said spacer is a plastic or a metal.

4. The method of claim 1, wherein said placing of said spacer is carried out before or after a protective sheath is placed over said catheter balloon.

5. The method of claim 1, further comprising removing said spacer after coating.

* * * * *